US00PP09526P

United States Patent [19]

Austin

[11] Patent Number: Plant 9,526

[45] Date of Patent: Apr. 30, 1996

[54] SHRUB ROSE PLANT NAMED 'AUSMAK'

[75] Inventor: David C. H. Austin, Albrighton, England

[73] Assignee: David Austin Roses Limited, England

[21] Appl. No.: 404,332

[22] Filed: Mar. 14, 1995

[30] Foreign Application Priority Data

May 20, 1994 [FR] France ..... 13477

[51] Int. Cl.[6] ..... A01H 5/00

[52] U.S. Cl. ..... Plt./1

[58] Field of Search ..... Plt./1, 22, 26

[56] References Cited

U.S. PATENT DOCUMENTS

| | | | |
|---|---|---|---|
| P.P. 7,215 | 4/1990 | Austin | Plt./1 |
| P.P. 8,153 | 2/1993 | Austin | Plt./1 |
| P.P. 8,157 | 2/1993 | Austin | Plt./1 |
| P.P. 8,789 | 6/1994 | Austin | Plt./1 |

*Primary Examiner*—Howard J. Locker

*Attorney, Agent, or Firm*—Klarquist Sparkman Campbell Leigh & Whinston

[57] ABSTRACT

A repeat flowering shurb rose having pale pink, scented, very full, old fashioned shaped flowers.

1 Drawing Sheet

The present invention relates to a new and distinct variety of rose plant of the shrub class which was originated by me by crossing an unnamed seedling with the variety Mary Rose.

The primary objective of this breeding was to produce a new rose variety having pink, scented, old fashioned shaped flowers on a repeat flowering bush. The objective was substantially achieved, along with other desirable improvements, as evidenced by the following unique combination of characteristics that are outstanding in the new variety and that distinguish it from its parents, as well as from all other varieties of which I am aware:

1. Very full flowers, 130–140 petals.
2. Pale pink flowers, with variation in tone across the flowers.
3. Quartered arrangement of petals.
4. Good repeat flowering qualities.

Asexual reproduction of this new variety by budding, as performed at Albrighton, Wolverhampton, England, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—Seedling.

*Pollen parent.*—Mary Rose.

Classification:

*Botanical.*—*Rosa hybrida.*

*Commercial.*—Shrub.

FLOWER

Observations made from specimens grown in a garden environment as Albrighton, Wolverhampton, England.

Blooming habit: Recurrent.

Bud:

*Size.*—About 2.5–3 cm long when the petals start to unfurl.

*Form.*—The bud form is pointed ovoid and globular.

*Color.*—When sepals first divide, bud color is Red Group 53B/C. When half blown, the upper sides of the petals are Red Group 49B/C; and the lower sides of the petals are Red Group 55D.

*Sepals.*—Color: Yellow-green Group 144A/B. Surface texture: Smooth, downy. There are three lightly appendaged sepals. There are two unappendaged sepals with smooth, downy edges.

*Receptacle.*—Color: Yellow-green Group 144A. Shape: Goblet. Size: Medium, about 8–10 mm long× 7–9 mm wide. Surface: Smooth.

*Peduncle.*—Length: Short-Medium, averaging about 3 cm. Surface: Glandular. Color: Medium green. Strength: Bending, heavy.

Bloom:

*Size.*—Medium, average open size is about 7.5 cm.

*Borne.*—In clusters of irregular shape.

*Stems.*—Medium, average length is about 60 cm.

*Form.*—When first open: Open cupped. Permanence: Flattens to rosette. Top of inner petals caught into calyx to form button.

*Petalage.*—Number of petals under normal conditions: 130–140.

*Color.*—The upper side of most of the outer petals is Red Group 56C; the inner petals are Red Group 49C. The reverse side of the petals is Red Group 56D. The base of each petal fades to white with a mid-yellow tip at the petal base. The major color on the upper side is Red 56 C.

*Variegations.*—None.

*Discoloration.*—The general tonality at the end of the first day: Paler, less red. At the end of the third day: Red Group 56D, but paler, fading to white.

*Fragrance.*—Moderate to strong rich tea rose.

Petals:

*Texture.*—Thin, soft.

*Shape.*—Notched slightly, deltoid.

*Form.*—Tips slightly recurved.

*Arrangement.*—Informal, with few petaloids in the center.

*Persistence.*—Petals tend to hang on and dry.

*Lastingness.*—On the plant: Short-fair, about 2–3 days. As a cut flower: Short-fair, about 2 days.

Reproductive parts:

*Anthers.*—Size: Medium. Quality: Few. Color: Yellow. Arrangement: Mixed with petaloids.

*Filaments.*—Color: Yellow.
*Pollen.*—Color: Gold yellow.
*Styles.*—Color: Greenish-white.
*Stigmas.*—Color: Yellow.

Form: Shrub.

Growth: Medium to vigorous. Mature plant is about 105 cm tall and 90 cm wide.

Foliage:

*Number of leaflets on normal mid-stem leaves.*—5 (sometimes 7).
*Size.*—Medium to large, about 17.5–18.5 cm long× 13–14 cm wide.
*Quantity.*—Normal.
*Color.*—New foliage: Yellow-green Group 144A with reddish blush. Old foliage: Yellow-green Group 147A.

Leaflets:

*Shape.*—Pointed oval.
*Texture.*—Upper side: Leathery.
*Edge.*—Serrated.
*Serration.*—Double, small.
*Petiole Rachis.*—Color: Green.
*Petiole underside.*—Rough, with prickles.
*Stipules.*—Long, serrated, about 3.5–4.0 cm long.
*Disease resistance.*—Resistant to mildew and black-spot under normal growing conditions at Albrighton, Wolverhampton, England.

Wood:

*New wood.*—Color: Light green, reddish. Bark: Smooth.
*Old Wood.*—Color: Green, streaky. Bark: Smooth.

Prickles:

*Quantity.*—On main canes from base: Ordinary. On laterals from main canes: Ordinary.
*Form.*—Medium to long, straight.
*Color when young.*—Red.

Small prickles:

*Quantity.*—On main stalks: Many. On laterals: Many.
*Color.*—Red.

I claim:

1. A new and distinct variety of rose plant of the shrub class, substantially as herein shown and described, characterized particularly as to novelty by the unique combination of its repeat flowering of pale pink, scented, very full, old fashioned shaped flowers, the petals of which are quartered.

* * * * *

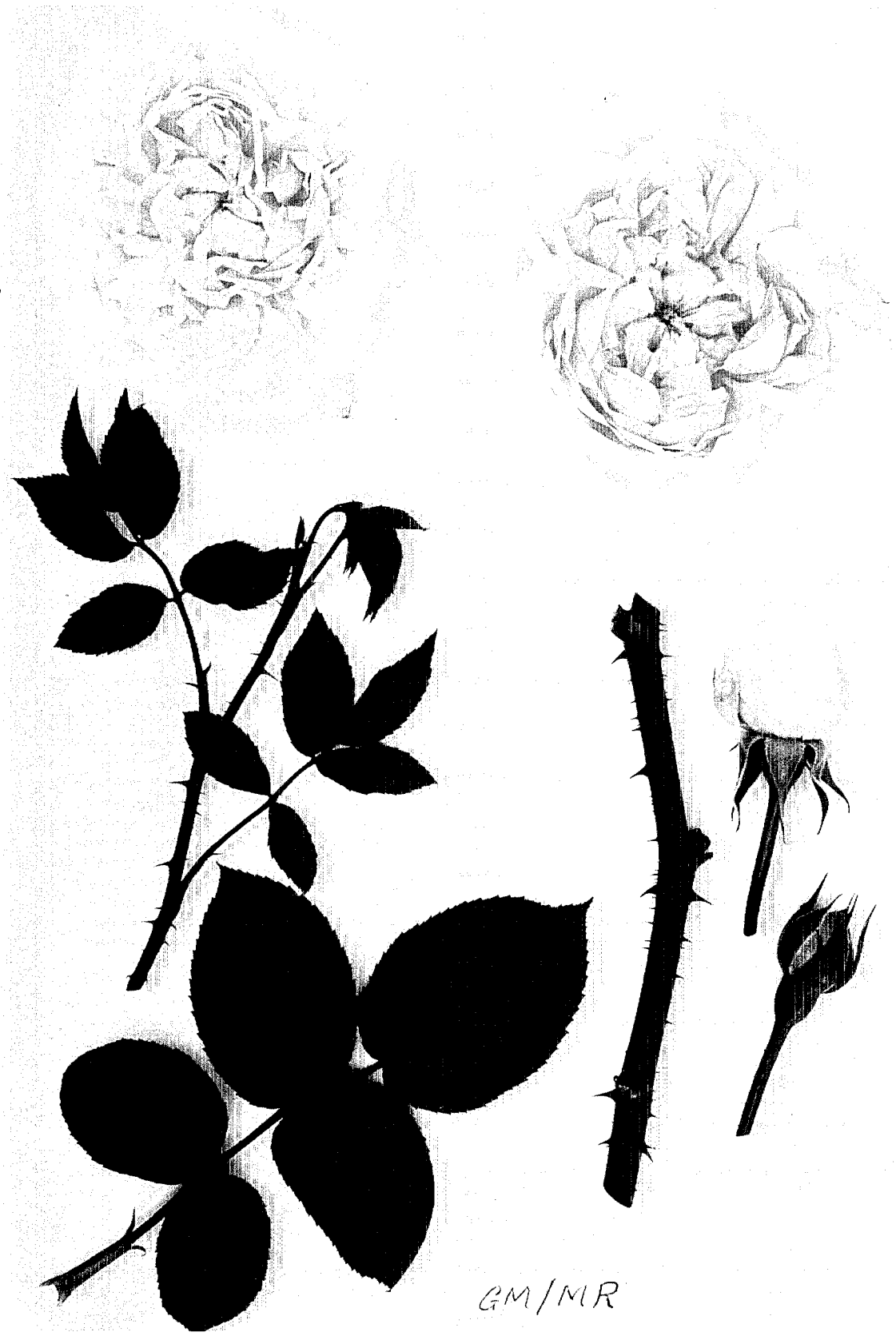
GM/MR

UNITED STATES PATENT AND TRADEMARK OFFICE

CERTIFICATE OF CORRECTION

PATENT NO. : PP 09,526
DATED : April 30, 1996
INVENTOR(S) : David C. H. Austin

It is certified that error appears in the above-indentified patent and that said Letters Patent is hereby corrected as shown below:

Title page, item [57]
In the Abstract:

Change "shurb" to --shrub--.

Col. 1, line 29; change "description" to --descriptions--.

Col. 1, line 42; change "as" to --at--.

Col. 2, line 18, after "60 cm." insert --Normal strength.--

Col. 2, line 21, after "button." add --Outer petal edges curl slightly.--

Col. 2, line 45, change "Quality" to -- Quantity--.

Signed and Sealed this
Eighth Day of April, 1997

*Attest:*

Bruce Lehman

BRUCE LEHMAN

*Attesting Officer*

*Commissioner of Patents and Trademarks*